United States Patent [19]

Evers

[11] Patent Number: Plant 7,333

[45] Date of Patent: Sep. 25, 1990

[54] ROSE PLANT TANCRESOR

[75] Inventor: Hans Evers, Ueterson, Fed. Rep. of Germany

[73] Assignee: Jackson & Perkins Company, Medford, Oreg.

[21] Appl. No.: 319,648

[22] Filed: Mar. 6, 1989

[51] Int. Cl.[5] ..... A01H 5/00

[52] U.S. Cl. ..... Plt./20

[58] Field of Search ..... Plt. 20, 21

*Primary Examiner*—Howard J. Locker

*Attorney, Agent, or Firm*—Majestic, Parsons, Siebert & Hsue

[57] ABSTRACT

A rose variety of the Hybrid Tea class is provided having production of many large red flowers, thick, leathery, long lived petals, large leathery foliage, vigorous, upright habit of growth and production of single bloom stems suitable for cutting.

1 Drawing Sheet

SUMMARY OF THE DISCOVERY

The present discovery relates to a new and distinct variety of rose plant of the Hybrid Tea class, which was originated by me by crossing the variety Precious Platinum with an unnamed seedling. The female parent, Precious Platinum, is a cardinal red, high centered, large hybrid tea with a very light fragrance. Its foliage is glossy, leathery and dark green. The male parent is an unnamed seedling with dark red flowers, very thick petals, long stems and leathery foliage.

The primary objective of this breeding was to produce a new rose variety of the Hybrid Tea class displaying abundant red flowers of large size on a vigorous plant. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Production of many large red flowers.
2. Thick, leathery, long lived petals.
3. Large leathery foilage.
4. Vigorous, upright habit of growth.
5. Production of single bloom stems suitable for cutting. The present discovery, a bright red hybrid tea, was selected as a seedling of the male and female parents' cross. Its color is midway between the parent colors. Flowers petals are thick like the male parent's, but the flower form is very close to that of the female parent. Foliage is similar to that of both parents.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE DISCOVERY

The following is a detailed description of my new rose cultivar, which has been denominated "Tancresor". Color terminology is in accordance with The Royal Horticultural Society Colour Chart except where an ordinary dictionary significance for the color is apparent.

Observations of the buds and flowers were made from specimens grown in a garden environment at Somis, Calif. in November.

Flower

The blooming habit is continuous. The bud size is one and one-quarter to one and three-eights inches when the petals start to unfurl. The bud form is a long pointed ovoid. The bud color when sepals first divide in near Red Group 44A; when half blown the upper side of the petals is near Red Group 42A, and the lower side of the petals is also near Red Group 42A. The sepals have a color near Yellow Green Group 147A. The surface texture is slightly rough, having small glandular structures on the outer surface. There are three lightly appendaged sepals, and two unappendaged sepals with hairy edges. The receptacle color is near Yellow Green Group 147A. The receptacle is of a very broad funnel shape, broad size and smooth surface. The peduncle is of medium length, with a prickly and glandular surface. Peduncle color is a bronzy light green, and the peduncle is stiff and erect. The flower opens slowly with a very double imbricated form. Flower production is quite high for a garden rose. In Somis, Calif., production of flowers is greater than popular garden red hydrid teas like Olympiad, Precious Platinum or Mr. Lincoln. This is because in Somis, the new Tancresor rose usually has 2 breaks from each stem cut or pruned, while Olympiad or Mr. Lincoln hybrid teas most often have a single break occurring from each stem. No actual flower counts are normally taken for garden roses.

Bloom

Bloom size is very large, with an average open size of four and one-half to five inches in diameter when the flower is fully expanded, borne singly. The stems are strong, and long averaging 16 to 18 inches in length from the first 5-leaflet leaf to the tip of the cracked open bud. The stems are excellent for cutting from the garden. The form when first opened is high center are retained to the end. The outer petal edges conditions there are 45 to 50 petals. The upper side of the petals at the flower center is near Red Group 42A, and the reverse side of the petals is near Red Group 42A. The base of petals is also near Red Group 42A, with a small yellow crescent. The major color on the upper side is near Red Group 42A. Variegations consist of white stripes on the petaloids running from petal base to tip. By the third day, there is a slight amount of bluing, as indicated by the color description.

There is no fragrance. The petal texture is leathery and round shaped. The form is moderately quilled.

The arrangement is imbricated with few petaloids in the center. The blooms drop off cleanly, and last both on the plant and as a cut flower for a long time. Hips normally do not form on this variety.

Reproductive Parts

There are many medium sized anthers of yellow color, arranged regularly around the styles, mixed with petaloids. The filaments are yellow or reddish brown, the pollen is lemon yellow, the styles are light red or deep pink and the stigmas are yellow.

Plant

A very vigorous, upright, branching growth of bush form. Plant height in California is 5 to 6 feet and habitually very upright. Plant width at maturity is 4 feet. This rose variety would survive outdoor temperatures of about 20° F. in winter. If colder temperatures are experienced in winter, some protection should be given to the bud union.

Foliage

Foliage is large sized and normal in quantity. The new foliage is reddish or bronzy colored. The old foliage is near Green Group 137A. Normal mid-stem leaves have five leaflets. Leaves vary in length, but average 6 inches long from the tip of the fifth leaflet to the point where the rachis is attached to the stem. The foliage is leathery in texture.

The leaflets are of a pointed oval shape and have a leathery texture with serrated edges. The serration is double and small in size. Petiole rachis is reddish green, and petiole underside has prickles. Stipules are medium and serrated. The foliage is susceptible to powdery mildew, but resistant to rust and moderatley resistant to blackspot under normal growing conditions at Somis, Calif.

Wood

New wood is reddish with a smooth bark. Old wood is green with a smooth bark.

Prickles

There are an ordinary number of prickles on main canes from the base and on laterals from the main canes. The form is long and hooked downward. There are few prickles on the main stalks or laterals. Colors when young and green and red, and becomes brown with age.

Parentage

The seed parent was of the variety Precious Platinum. The pollen parent was an unnamed seedling.

Classification

Botanical is Rosa hybrid. Commercial is Hybrid tea.

I claim:

1. A new and distinct variety of rose plant of the Hybrid Tea class substantially as herein shown and described, characterized particularly as to novelty by the unique combination of outstanding vigor, upright habit of growth, leathery foliage, thick petals and abundant large red flowers.

* * * * *

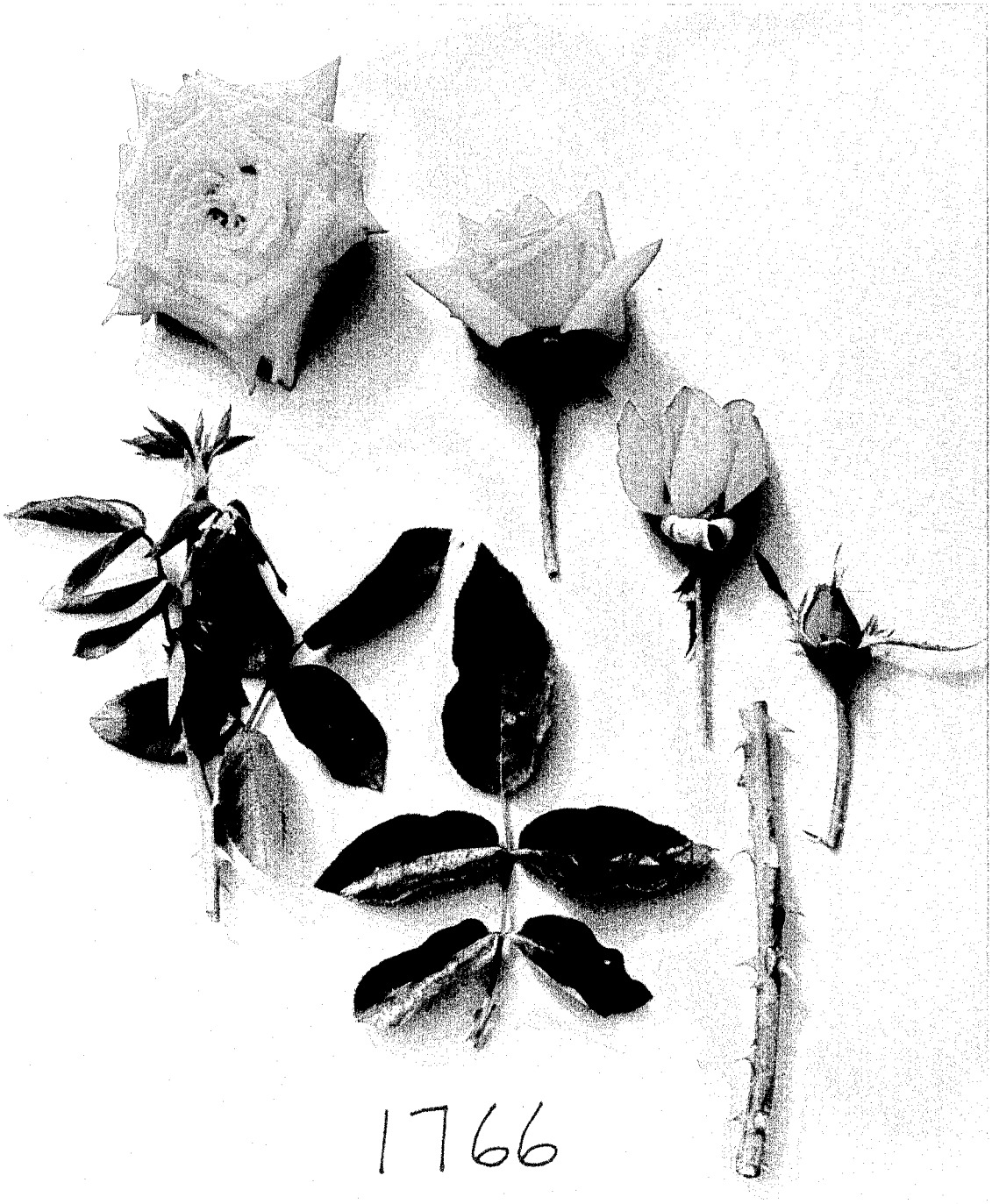
1766